US012639833B2

(12) United States Patent
Li et al.

(10) Patent No.: US 12,639,833 B2
(45) Date of Patent: May 26, 2026

(54) AUTOMATIC ALIGNMENT OF TWO PULLBACKS

(71) Applicant: LightLab Imaging, Inc., Westford, MA (US)

(72) Inventors: Shimin Li, Acton, MA (US); Ajay Gopinath, Bedford, MA (US)

(73) Assignee: LightLab Imaging, Inc., Westford, MA (US)

( * ) Notice: Subject to any disclaimer, the term of this patent is extended or adjusted under 35 U.S.C. 154(b) by 317 days.

(21) Appl. No.: 18/292,188

(22) PCT Filed: Jul. 6, 2022

(86) PCT No.: PCT/US2022/036228
§ 371 (c)(1),
(2) Date: Jan. 25, 2024

(87) PCT Pub. No.: WO2023/014461
PCT Pub. Date: Feb. 9, 2023

(65) Prior Publication Data
US 2024/0346670 A1 Oct. 17, 2024

Related U.S. Application Data

(60) Provisional application No. 63/229,702, filed on Aug. 5, 2021.

(51) Int. Cl.
*G06T 7/33* (2017.01)
*A61B 8/00* (2006.01)
*A61B 8/12* (2006.01)

(52) U.S. Cl.
CPC .................. *G06T 7/33* (2017.01); *A61B 8/12* (2013.01); *A61B 8/463* (2013.01); *G06T 2207/30101* (2013.01)

(58) Field of Classification Search
CPC ... A61B 5/0066; A61B 5/0084; A61B 5/6852; A61B 6/4417; A61B 6/5247; A61B 8/12;
(Continued)

(56) References Cited

U.S. PATENT DOCUMENTS 6,095,976 A * 8/2000 Nachtomy .......... G01S 7/52046
600/443
7,593,559 B2 9/2009 Toth et al.
(Continued)

OTHER PUBLICATIONS

Dong et al. "Integrated electroanatomic mapping with three-dimensional computed tomographic images for real-time guided ablations." Circulation 113.2 (2006): 186-194. (Year: 2006).*
(Continued)

*Primary Examiner* — Katrina R Fujita
(74) *Attorney, Agent, or Firm* — Lerner David LLP

(57) ABSTRACT

The present disclosure provides systems and methods for automatically aligning intravascular data taken during a plurality of pullbacks in a target blood vessel. Extraluminal images may be taken to determine the location of the guide catheter in the target vessel. Two or more pullbacks may then be performed in the target vessel. The start and end point of each pullback may be determined. A distance between the end point of each pullback and the proximal tip, or junction point, of the guide catheter may be determined. A difference between the end point of each pullback and the junction point may be determined. The difference between the distances from the end of the pullback and the junction point may correspond to the distance to offset one of the representations of the pullbacks in order to automatically align the representation of the pullbacks.

20 Claims, 7 Drawing Sheets

(58) Field of Classification Search
CPC ..... A61B 8/4416; A61B 8/463; A61B 8/5246; A61B 8/5261; G06T 7/33; G06T 2207/30101
See application file for complete search history.

(56) References Cited

U.S. PATENT DOCUMENTS

| | | | | |
|---|---|---|---|---|
| 9,907,527 | B2 * | 3/2018 | Dascal | A61B 6/504 |
| 2012/0059253 | A1 | 3/2012 | Wang et al. | |
| 2014/0094692 | A1 | 4/2014 | Tolkowsky et al. | |
| 2014/0270436 | A1 * | 9/2014 | Dascal | A61B 5/0073 |
| | | | | 382/130 |
| 2016/0093049 | A1 * | 3/2016 | Kobayashi | A61B 5/0035 |
| | | | | 382/131 |
| 2019/0307514 | A1 * | 10/2019 | Schwartz | A61B 5/06 |
| 2019/0339850 | A1 | 11/2019 | Ho | |
| 2022/0061670 | A1 * | 3/2022 | Petroff | A61B 5/0044 |

OTHER PUBLICATIONS

Hagenaars et al. "Reproducibility of volumetric quantification in intravascular ultrasound images." Ultrasound in medicine & biology 26.3 (2000): 367-374. (Year: 2000).*
Mallas et al. "Progress on multimodal molecular/anatomical intravascular imaging of coronary vessels combining near infrared fluorescence and ultrasound." 2011 Annual International Conference of the IEEE Engineering in Medicine and Biology Society. IEEE, 2011. (Year: 2011).*

Ughi et al. "Dual modality intravascular optical coherence tomography (OCT) and near-infrared fluorescence (NIRF) imaging: a fully automated algorithm for the distance-calibration of NIRF signal intensity for quantitative molecular imaging." international journal of cardiov. img. 31.2 (2015): 259-268 (Year: 2015).*
Verma et al. "Localization of fossa ovalis and Brockenbrough needle prior to left atrial ablation using three-dimensional mapping with EnSite Fusion™." Journal of Interventional Cardiac Electrophysiology 30.1 (2011): 37-44. (Year: 2011).*
Zhang et al. "Simultaneous registration of location and orientation in intravascular ultrasound pullbacks pairs via 3D graph-based optimization." IEEE transactions on medical imaging 34.12 (2015): 2550-2561. (Year: 2015).*
Hagenaars T et al: "Reproducibility of volumetric quantification in intravascular ultrasound images", Ultrasound in Medicine and Biology, New York, NY, US, vol. 26, No. 3, Mar. 1, 2000 (Mar. 1, 2000), pp. 367-374, XP004295524, ISSN: 0301-:5629, DOI: 10.1016/S0301-5629(99)00141~6 p. 369, left-hand column first paragraph, Analysis.
International Search Report and Written Opinion issued in Appln. No. PCT/US2022/036228 dated Oct. 17, 2022 (11 pages).
Liu, S., et al., "Histogram-based standardization of intravascular optical coherence tomography images acquired from different imaging systems". Med. Phys., 45: 4158-4170 (Jul. 2018). https://doi.org/10.1002/mp.13103.
Terumo Corporation, "Lunawave" (Aug. 2013). 2 pgs.
Communication pursuant to Rules 161(1) and 162 EPC for European Application No. 22751515.2 dated Mar. 13, 2024. 3 pgs.

* cited by examiner

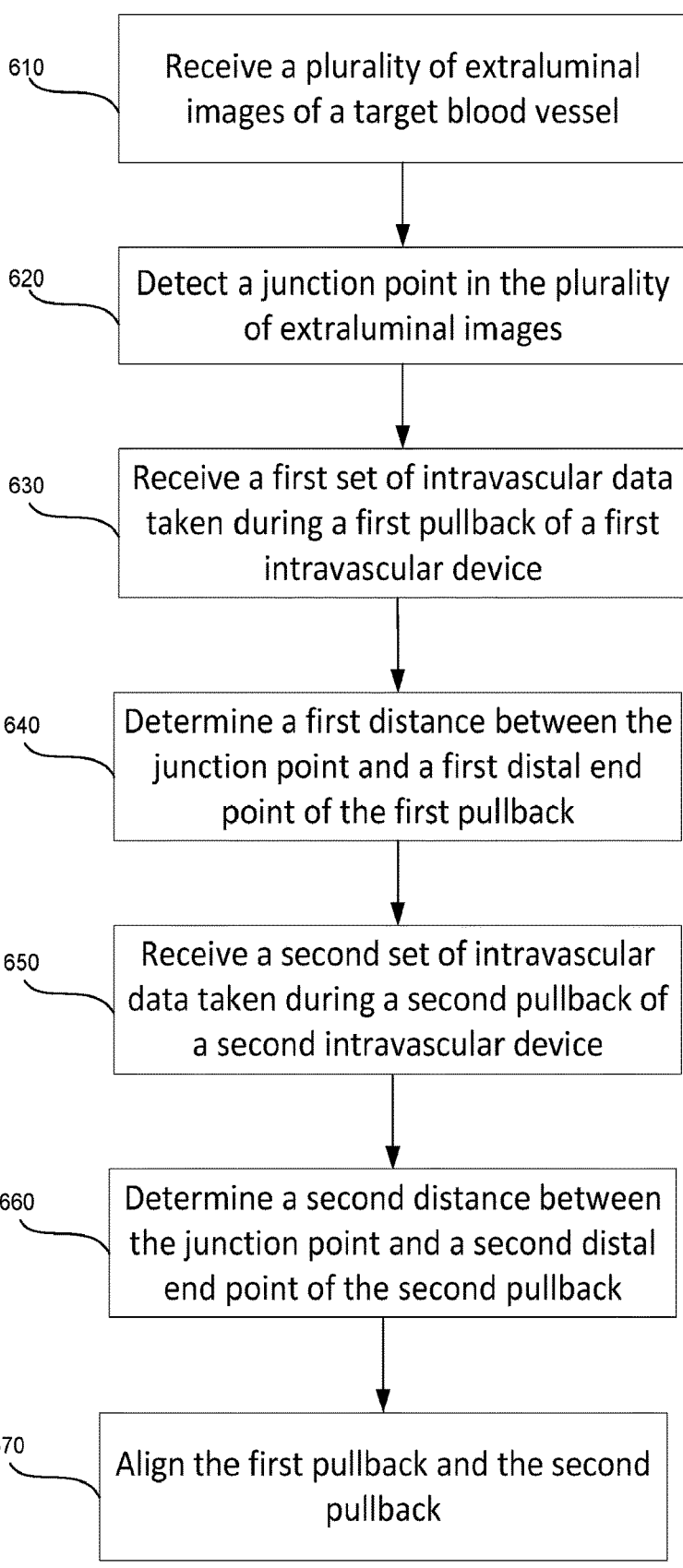

610   Receive a plurality of extraluminal images of a target blood vessel

620   Detect a junction point in the plurality of extraluminal images

630   Receive a first set of intravascular data taken during a first pullback of a first intravascular device 640   Determine a first distance between the junction point and a first distal end point of the first pullback 650   Receive a second set of intravascular data taken during a second pullback of a second intravascular device 660   Determine a second distance between the junction point and a second distal end point of the second pullback 670   Align the first pullback and the second pullback

FIG. 6

AUTOMATIC ALIGNMENT OF TWO PULLBACKS

CROSS-REFERENCE TO RELATED APPLICATIONS

This application is a national phase entry under 35 U.S.C. § 371 of International Application No. PCT/US2022/036228, filed Jul. 6, 2022, which claims the benefit of the filing date of U.S. Provisional Application No. 63/229,702, filed Aug. 5, 2021, entitled Automatic Alignment of Two Pullbacks, the disclosures of which are hereby incorporated herein by reference.

BACKGROUND

Intravascular data can be obtained by performing one or more pullbacks of an intravascular device. The intravascular device may be an optical coherence tomography ("OCT") probe, an intravascular ultrasound ("IVUS") imaging probe, a pressure wire, etc. A pre-intervention pullback may be performed before coronary intervention, such as a stent implantation, and a post-intervention pullback may be performed afterwards. Aligning the representation of the pre-intervention pullback with the representation of the post-intervention pullback requires a user to manually identify corresponding points on each pullback, which may lead to errors. For example, the user may misidentify points as corresponding points on each of the pullback, which would lead to the representations of each pullback being mis-aligned.

BRIEF SUMMARY

The disclosure is generally directed to automatically aligning representations of intravascular data obtained during two or more pullbacks. The pullbacks may be performed using the same and/or different modalities. For example, a first pullback may record intravascular images and a second pullback may record intravascular data measurements, such as pressure measurements. A representation of each of the pullbacks may be vertically aligned such that corresponding segments of the vessel in which the pullbacks were performed are vertically aligned.

One or more extraluminal images, such as angiograms, x-rays, or the like, may be taken before, during, or after a guide catheter is inserted into a target vessel. A plurality of pullbacks may be performed by a physician using, for example, an OCT probe, IVUS probe, pressure wire, micro-OCT probe, near-infrared spectrometry (NIRS) sensor, etc. A distance between an end point of each pullback and a proximal tip of the catheter may be determined, for example, by measuring the pixels between the end of each pullback and the proximal tip of the catheter. The start point of each pullback may be a distal-most point where intravascular data is captured, and the end point may be a proximal-most point. The proximal tip of the catheter may be, in some examples, referred to as a junction point, wherein the junction point is where the catheter and the guide wire meet. In some examples, the junction point is a point that is the same for each pullback. For example, the catheter may not move between each pullback such that the proximal tip of the catheter, or the junction point, is in the same location for each pullback. A difference between the end point of each pullback and the junction point may be determined, for example, by subtracting the distance of the end of the first pullback to the junction point from the distance of the end of the second pullback to the junction point. Such difference may correspond to an offset distance, the offset distance being a distance by which an end point of the representation of the second pullback is horizontally offset from an end point of the representation of the first pullback when the first and second representations are vertically aligned at the junction point. For example, if the second pullback has an end point further way from the junction point than the first pullback, the end point of the representation of the second pullback may be horizontally offset from the end point of the representation of the first pullback by the offset difference.

Aspects of the disclosed technology can include any combination of the features described herein.

One aspect of the disclosure provides a method, comprising receiving, by one or more processors, a plurality of extraluminal images of a target blood vessel, detecting, by the one or more processors, a junction point in the plurality of extraluminal images, receiving, by the one or more processors, a first set of intravascular data taken during a first pullback of a first intravascular device, determining, by the one or more processors, a first distance between the junction point and a first distal end point of the first pullback, receiving, by the one or more processors, a second set of intravascular data taken during a second pullback of a second intravascular device, determining, by the one or more processors, a second distance between the junction point and a second distal end point of the second pullback; and aligning, by the one or more processors based on the first distance and the second distance, a first representation of the first set of intravascular data with a second representation of the second set of intravascular data. The method may further include outputting for display, by the one or more processors, the first representation and the second representation, wherein first representation is vertically aligned with the second representation. Aligning the first representation and the second representation may include determining, by the one or more processors, a difference between the second distance and the first distance, and horizontally offsetting, by the one or more processors based on the determined difference, a distal end of the second representation from a distal end of the first representation. The junction point may be a proximal point of the guide catheter. The first intravascular may be the same device as the second intravascular device. The first and second sets of intravascular data may include intravascular images. The plurality of extraluminal images may be taken during both the first pullback and the second pullback. Detecting the junction point may further include determining, by the one or more processors based on the plurality of extraluminal images, the set of intravascular data, or the second set of intravascular data, at least one artificial intelligence ("AI") mask. Determining the first distal end point of the first pullback and the second distal end point of the second pullback may further include determining, based on the plurality of extraluminal images, the first set of intravascular data, or the second set of intravascular data, at least one wire mask image frame. According to some examples, the method may further include co-registering, by the one or more processors, the first set of intravascular data and the second set of intravascular data to the plurality of extraluminal images.

Another aspect of the disclosure provides a device, comprising one or more processors, The one or more processors may be configured to receive a plurality of extraluminal images of a target blood vessel, detect a junction point in the plurality of extraluminal images, receive a first set of intravascular data taken during a first pullback of a first intravascular device, determine a first distance between the junction point and a first distal end point of the first pullback, receive a second set of intravascular data taken during a second pullback of a second intravascular device, determine a second distance between the junction point and a second distal end point of the second pullback, and align, based on the first distance and the second distance, a first representation of the first set of intravascular data with a second representation of the second set of intravascular data. The one or more processors may be further configured to output for display the first representation and the second representation, wherein first representation is vertically aligned with the second representation. When aligning the first representation and the second representation the one or more processors may be further configured to determine a difference between the second distance and the first distance, and horizontally offset, based on the determined difference, a distal end of the second representation from a distal end of the first representation. The junction point may be a proximal point of the guide catheter. The first intravascular device may be the same device as the second intravascular device. The first and second sets of intravascular data may include intravascular images. The plurality of extraluminal images may be taken during both the first pullback and the second pullback. When detecting the junction point, the one or more processors may be further configured to determine, based on the plurality of extraluminal images, the set of intravascular data, or the second set of intravascular data, at least one artificial intelligence ("AI") mask. When determining the first distal end point of the first pullback and the second distal end point of the second pullback, the one or more processors may be further configured determine, based on the plurality of extraluminal images, the first set of intravascular data, or the second set of intravascular data, at least one wire mask image frame. The one or more processors may be further configured to co-register the first set of intravascular data and the second set of intravascular data to the plurality of extraluminal images.

BRIEF DESCRIPTION OF THE DRAWINGS

FIG. 6 is a flow diagram illustrating a method of aligning a representation of intravascular data obtained during a first and second pullback according to aspects of the disclosure.

DETAILED DESCRIPTION

Figure 1A:
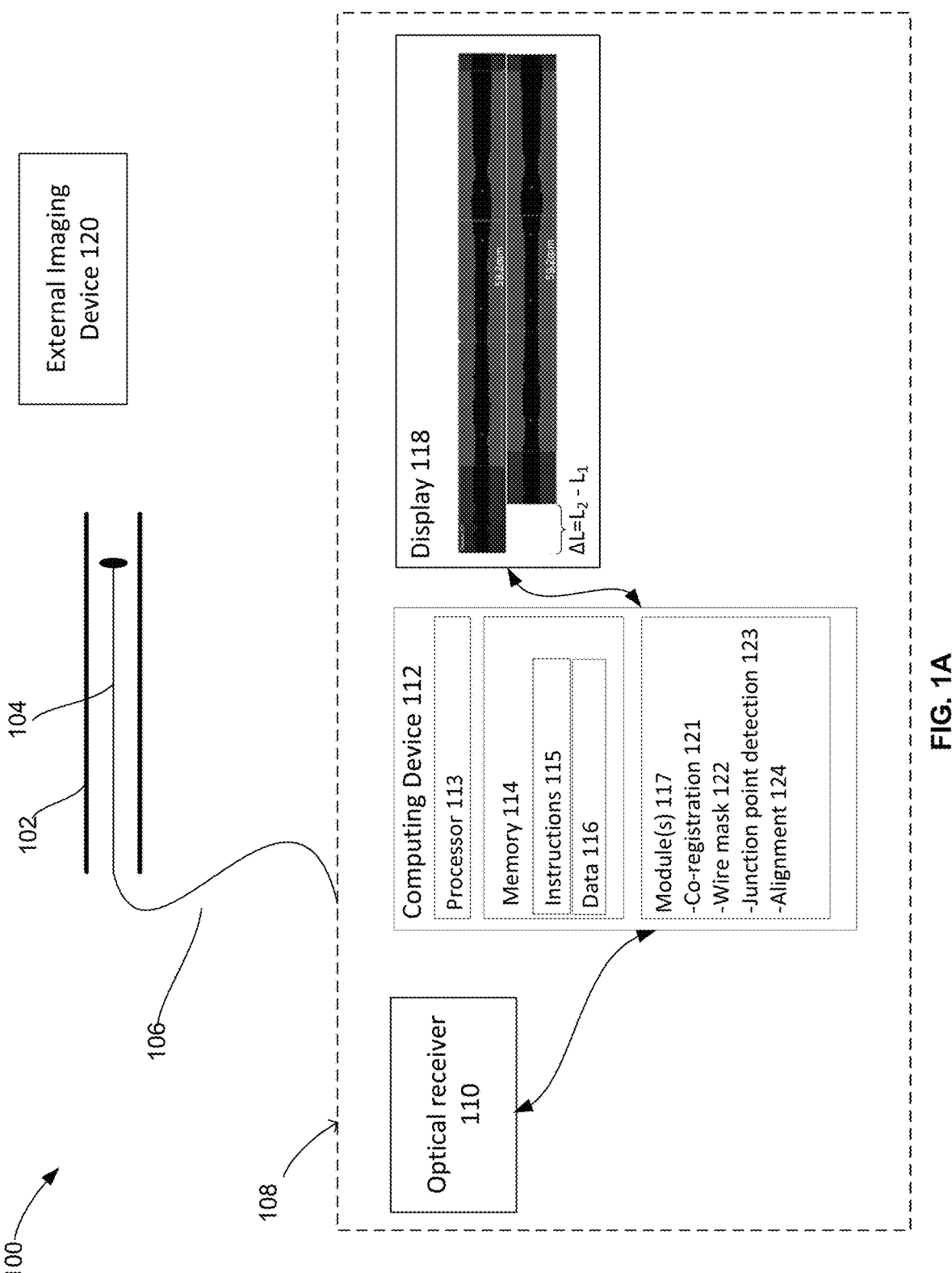
FIG. 1A is an example system according to aspects of the disclosure.

FIG. 1A illustrates a data collection system 100 for use in collecting intravascular and extravascular data. The system may include a data collection probe 104. The data collection probe 104 may be, for example, an OCT probe, an IVUS catheter, micro-OCT probe, near infrared spectroscopy (NIRS) sensor, or any other device that can be used to image a blood vessel 102. In some examples, the data collection probe 104 may be a pressure wire, a flow meter, etc. While the examples provided herein refer to an intravascular imaging device, such as an OCT probe, the use of an OCT probe is not intended to be limiting. For example, an IVUS catheter, a pressure wire, or another intravascular data collection device may be used in conjunction with or instead of the OCT probe. A guidewire, not shown, may be used to introduce the probe 104 into the blood vessel 102. The probe 104 may be introduced and pulled back along a length of a blood vessel while collecting data. The intravascular data sets, or frames of image data, may be used to identify features, such as the cross-sectional area of the bolus.

The probe 104 may be connected to a subsystem 108 via an optical fiber 106. The subsystem 108 may include a light source, such as a laser, an interferometer having a sample arm and a reference arm, various optical paths, a clock generator, photodiodes, and other OCT, IVUS, micro-OCT, NIRS, and/or pressure wire components.

The probe 104 may be connected to an optical receiver 110. According to some examples, the optical receiver 110 may be a balanced photodiode based system. The optical receiver 110 may be configured to receive light collected by the probe 104. The probe 104 may be coupled to the optical receiver 110 via a wired or wireless connection.

The system 100 may further include, or be configured to receive data from, an external imaging device 120. The external imaging device may be, for example, an imaging system based on angiography, fluoroscopy, x-ray-, nuclear magnetic resonance, computer aided tomography, etc. The external imaging device 120 may be configured to noninvasively image the blood vessel 102. According to some examples, the external imaging device 120 may obtain one or more images before, during, and/or after a pullback of the data collection probe 104.

The external imaging device 120 may be in communication with subsystem 108. According to some examples, the external imaging device 120 may be wirelessly coupled to subsystem 108 via a communications interface, such as Wi-Fi or Bluetooth. In some examples, the external imaging device 120 may be in communication with subsystem 108 via a wire, such as an optical fiber. In yet another example, external imaging device 120 may be indirectly communicatively coupled to subsystem 108 or computing device 112. For example, the external imaging device 120 may be coupled to a separate computing device (not shown) that is in communication with computing device 112. As another example, image data from the external imaging device 120 may be transferred to the computing device 112 using a computer-readable storage medium.

The subsystem 108 may include a computing device 112. One or more steps may be performed automatically or without user input to navigate images, input information, select and/or interact with an input, etc. In some examples, one or more steps may be performed based on receiving a user input by mouse clicks, a keyboard, touch screen, verbal commands, etc.

The computing device may include one or more processors 113, memory 114, instructions 115, data 116, and one or more modules 117.

The one or more processors 113 may be any conventional processors, such as commercially available microprocessors. Alternatively, the one or more processors may be a dedicated device such as an application specific integrated circuit (ASIC) or other hardware-based processor. Although FIG. 1 functionally illustrates the processor, memory, and other elements of device 110 as being within the same block, it will be understood by those of ordinary skill in the art that the processor, computing device, or memory may actually include multiple processors, computing devices, or memories that may or may not be stored within the same physical housing. Similarly, the memory may be a hard drive or other storage media located in a housing different from that of device 112. Accordingly, references to a processor or computing device will be understood to include references to a collection of processors or computing devices or memories that may or may not operate in parallel.

Memory 114 may store information that is accessible by the processors, including instructions 115 that may be executed by the processors 113, and data 116. The memory 114 may be a type of memory operative to store information accessible by the processors 113, including a non-transitory computer-readable medium, or other medium that stores data that may be read with the aid of an electronic device, such as a hard-drive, memory card, read-only memory ("ROM"), random access memory ("RAM"), optical disks, as well as other write-capable and read-only memories. The subject matter disclosed herein may include different combinations of the foregoing, whereby different portions of the instructions 115 and data 116 are stored on different types of media.

Memory 114 may be retrieved, stored or modified by processors 113 in accordance with the instructions 115. For instance, although the present disclosure is not limited by a particular data structure, the data 116 may be stored in computer registers, in a relational database as a table having a plurality of different fields and records, XML documents, or flat files. The data 116 may also be formatted in a computer-readable format such as, but not limited to, binary values, ASCII or Unicode. By further way of example only, the data 116 may be stored as bitmaps comprised of pixels that are stored in compressed or uncompressed, or various image formats (e.g., JPEG), vector-based formats (e.g., SVG) or computer instructions for drawing graphics. Moreover, the data 116 may comprise information sufficient to identify the relevant information, such as numbers, descriptive text, proprietary codes, pointers, references to data stored in other memories (including other network locations) or information that is used by a function to calculate the relevant data.

The instructions 115 can be any set of instructions to be executed directly, such as machine code, or indirectly, such as scripts, by the processor 113. In that regard, the terms "instructions," "application," "steps," and "programs" can be used interchangeably herein. The instructions can be stored in object code format for direct processing by the processor, or in any other computing device language including scripts or collections of independent source code modules that are interpreted on demand or compiled in advance. Functions, methods and routines of the instructions are explained in more detail below.

The modules 117 may include a co-registration module, a wire mask module, a junction point detection module, and an alignment module.

The computing device 112 may be adapted to co-register intravascular data with a luminal image. For example, computing device 112 may access co-registration module 121 to co-register the intravascular data with the luminal image. The luminal image may be an extraluminal image, such as an angiograph, x-ray, or the like. The co-registration module 121 may co-register intravascular data, such as an intravascular image, pressure readings, virtual flow reserve ("VFR"), fractional flow reserve ("FFR"), resting full-cycle ration ("RFR"), flow rates, etc. with the extraluminal image. In some examples, the co-registration module 121 may co-register intravascular data with an intraluminal image, such as an intraluminal image captured by an OCT probe, IVUS probe, micro-OCT probe, or the link.

In one example, the co-registration module 121 may co-register intraluminal data captured during a pullback with one or more extraluminal images. For example, the extraluminal image frames may be pre-processed. Various matrices such as convolution matrices, Hessians, and others can be applied on a per pixel basis to change the intensity, remove, or otherwise modify a given angiography image frame. As discussed herein, the preprocessing stage may enhance, modify, and/or remove features of the extraluminal images to increase the accuracy, processing speed, success rate, and other properties of subsequent processing stages. A vessel centerline may be determined and/or calculated. In some examples, the vessel centerline may be superimposed or otherwise displayed relative to the pre-processed extraluminal image. According to some examples, the vessel centerline may represent a trajectory of the collection probe 104 through the blood vessel during a pullback. In some examples, the centerline may be referred to as a trace. Additionally or alternatively, marker bands or radiopaque markers may be detected in the extraluminal image frames. According to some examples, the extraluminal image frames and the data received by collection probe 104 may be co-registered based on the determined location of the marker bands.

The computing device 112 may be adapted to determine a wire mask of an extraluminal image. For example, the computing device 112 may access a wire mask module 122 to determine, or create, a wire mask image frame of the extraluminal image. According to some examples, the wire mask module 122 may process the extraluminal images to determine, or create, a mask of a catheter and/or guidewire within the vessel.

Determining a wire mask image frame may include smoothing the image, such as by normalizing one or more image frames. Normalizing the image frames may convert the pixels in the image frame into a numerical range between zero (0) and one (1). According to some examples, normalizing the image frames allows the trained AI network to recognize the pixels as various structures, such as the catheter and guide wire. Smoothing the extraluminal image may enhance elongated structures in image. According to some examples, the structures being elongated include one or more of vessels, guidewires, ribs, the catheter, or other edge containing elements in the image.

In some examples, one or more morphological filters may be applied to the image to eliminate wide structures in the image. Wide structures may be, for example, bone structures in the image frames. According to some examples, the morphological filter may be a bottom hat filter or any filter configured or constrained to enhance or select small scale features, such as thin elements. The morphological filter allows for the enhancement of dark elongated elements in the image that have typical scale to the structure element used in a given morphological filter, such as for example, a bottom hat filter. In some examples, the morphological filter can be replaced by a median filter to produce a similar result.

In some examples, a ridge enhancing filter or detector or a vessel segmentation filter may be applied to the image. The ridge enhancing filter may be a Frangi filter, a Hessian filter, or other ridge or edge detectors. The ridge enhancing filter may extract thin elongated features in the image. The ridge enhancing filter output may be thresholded to produce a binary image containing thin and elongated dark elements that appear as bright pixels in the thresholded image.

In some examples, after thresholding the ridge enhanced image, adaptive thresholding may be performed on the image. An adaptive binary threshold may be applied in order to reject image areas with intensity values that are not of interest. In some examples, bright areas that have an intensity greater than a threshold associated with an intensity value or range of values corresponding to dark values may be rejected.

The thresholded ridge enhanced image and the image produced after applying the adaptive binary threshold may be merged using a pixel-wise AND operator, to obtain a merged metallic wire mask component. The wire mask module 122 may then connect and filter wire fragments that are detected in the images.

The guidewire may be extracted in fragments and other components, such as the catheter, junction point, and/or markers on the guidewire, may be detected. The wire fragments may be joined using a combined measurement of a takeoff angle and a distance between the fragments.

According to some examples, the wire mask module 122 may perform post filtering of components and/or thinning of components may be performed to remove elements from the surrounding area that may have joined during the wire detection.

The wire mask module 122 may output and/or store in memory 114 a wire mask of the detected catheter 202, guidewire 204, and/or junction point 206.

The computing device 112 may be adapted to determine the location of the proximal point of a guide catheter in one or more image frames. The proximal point of the guide catheter may be the junction point. For example, the computing device 112 may access a junction point detection module 123 to determine the location. According to some examples, the junction point detection module 123 may determine the location of the junction point using the wire mask output by wire mask module 122.

Figure 1B:
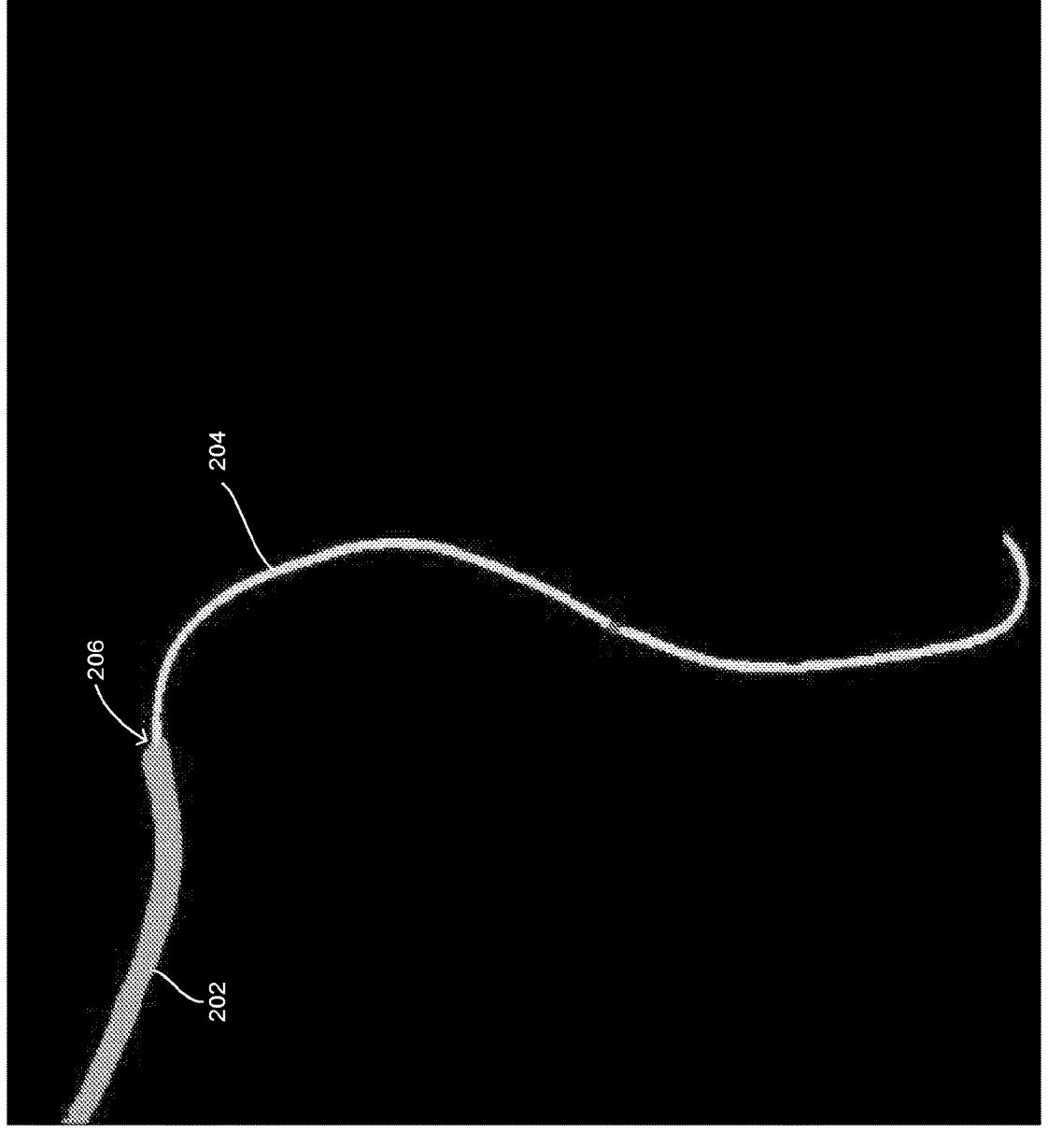
FIG. 1B is an example AI mask according to aspects of the disclosure.

In some examples, the junction point detection module 123 may determine the location of the junction point using a trained artificial intelligence ("AI") network. The AI network may be trained using one or more extraluminal images and/or annotations as input. The extraluminal images may be, for example, angiography image, CT images, MRI images, etc. The annotations may be annotations identifying the location of the proximal tip of the catheter and/or the location of the guidewire. The trained AI network may output an AI mask, as shown in FIG. 1B. The AI mask 100A may identify the catheter and/or the guidewire in the image. The AI mask 100A may additionally or alternatively identify the junction point 206. The junction point may be, for example, the proximal tip of catheter 202. In some examples, the junction point 206 is the location where catheter 202 and guide wire 204 meet or intersect. The junction point detection module 123 may be used the trained AI network to predict and/or identify the location of the junction point on subsequent image frames.

The computing device 112 may be adapted to align representations of two or more pullbacks. For example, computing device 112 may access alignment module 124 to align the representations. The alignment of the representations of two or more pullbacks further include vertically aligning a portion of a first representation to a portion of the second representation. The portion of the first representation and the second representation may correspond to the junction point, a location in the pullback, etc. Thus, the portion of the first representation and the second longitudinal may correspond to the same location in the vessel.

In some examples, to vertically align the representations such that portions of each representation corresponding to the same location within the vessel are vertically aligned, alignment module 124 may determine an offset distance. The offset distance may be a difference in the distance between the end of the first pullback and the junction point "L1" and the distance between the end of the second pullback and the junction point "L2". For example, the difference "ΔL" may be calculated by subtracting "L1" from "L2." The difference between the ends of each pullback and the junction point may be the offset distance in which the second longitudinal representation is horizontally offset when vertically aligned with the first longitudinal representation.

According to some examples, the modules made additionally or alternatively include a video processing software module, a preprocessing software module, an image file size reduction software module, a catheter removal software module, a shadow removal software module, a vessel enhancement software module, a blob enhancement software module, a Laplacian of Gaussian filter or transform software module, a guidewire detection software module, an anatomic feature detection software module, stationary marker detection software module, a background subtraction module, a Frangi vesselness software module, an image intensity sampling module, a moving marker software detection module, iterative centerline testing software module, a background subtraction software module, a morphological close operation software module, a feature tracking software module, a catheter detection software module, a bottom hat filter software module, a path detection software module, a Dijkstra software module, a Viterbi software module, fast marching method based software modules, a vessel centerline generation software module, a vessel centerline tracking module software module, a Hessian software module, an intensity sampling software module, a superposition of image intensity software module and other suitable software modules as described herein.

The subsystem 108 may include a display 118 for outputting content to a user. The display 118 may be integrated with the computing device 112, or it may be a standalone unit electronically coupled to the computing device 112. The display 118 may output intravascular data relating to one or more features detected in the blood vessel and/or obtained during a pullback. For example, the output may include, without limitation, cross-sectional scan data, longitudinal scans, diameter graphs, image masks, lumen border, plaque sizes, plaque circumference, visual indicia of plaque location, visual indicia of risk posed to stent expansion, flow rate, etc. The display 118 may identify features with text, arrows, color coding, highlighting, contour lines, or other suitable human or machine-readable indicia.

According to some examples the display 118 may include a graphic user interface ("GUI"). The display 118 may be a touchscreen display in which a user can provide an input to navigate images, input information, select and/or interact with an input, etc. In some examples, the display 118 and/or computing device 112 may include an input device, such as a trackpad, mouse, keyboard, etc. that allows a user to navigate images, input information, select and/or interact with an input, etc. The display 118 alone or in combination with computing device 112 may allow for toggling between one or more viewing modes in response to user inputs. For example, a user may be able to toggle between different intravascular data, images, etc. recorded during each of the pullbacks.

In some examples, the display 118, alone or in combination with computing device 112, may present one or more menus as output to the physician, and the physician may provide input in response by selecting an item from the one or more menus. For example, the menu may allow a user to show or hide various features. As another example, there may be a menu for selecting blood vessel features to display.

The output may include aligned representations of intravascular data received from a plurality of pullbacks. For example, each pullback may be output as a longitudinal representation of the vessel, a graphical representation of the intravascular data, etc. According to some examples, the representation of the first pullback and the representation of the second pullback may be vertically aligned. The intravascular data from each of the pullbacks may be aligned based on a difference between the end of each pullback and the junction point, as discussed herein with respect to FIG. 5. For example, a first pullback may end a distance "L1" from the junction point and a second pullback may end a distance "L2" from the junction point. The difference "ΔL" between "L2" and "L1" may be the distance that the end of the representation of the second pullback is horizontally offset from the end of the representation of the first pullback.

Figure 2B:
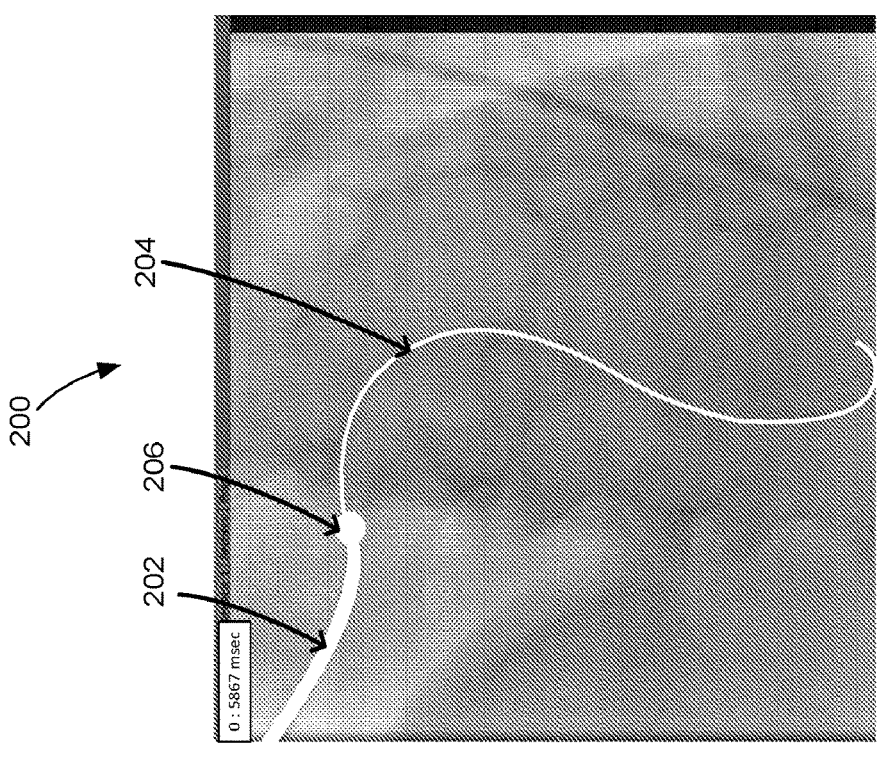
FIGS. 2A and 2B are example extravascular images according to aspects of the disclosure.
Figure 2A:
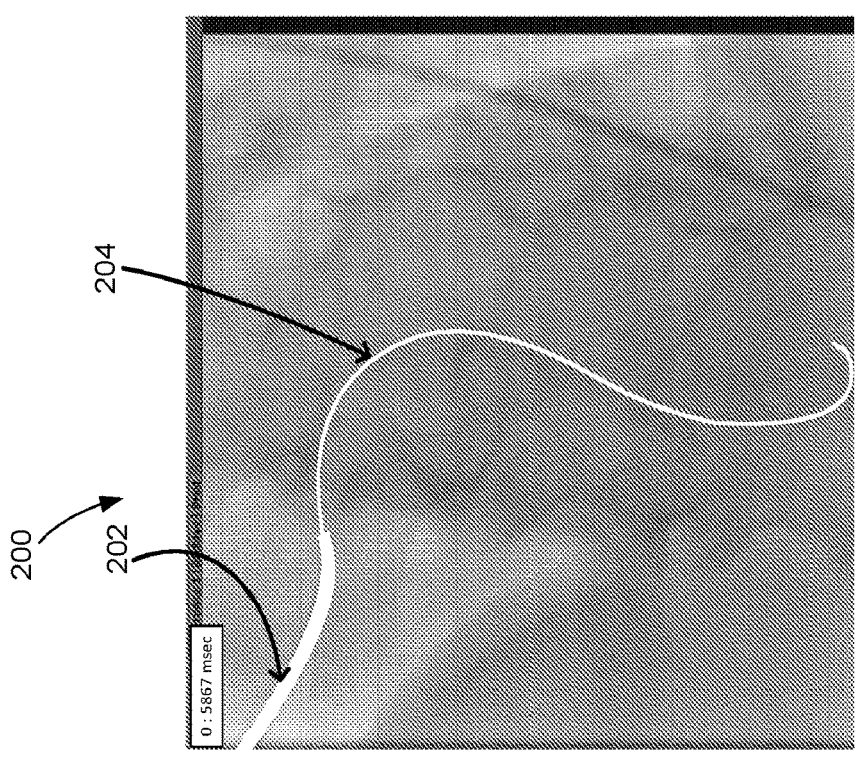

FIG. 2A illustrates an image obtained by external imaging device 120. The image 200 may be one of a plurality of angiography images taken by external imaging device. In an example where the image 200 is an angiography image, the image 200 may be obtained before contrast is injected into the blood vessel, while contrast is injected into the blood vessel, or after contrast is injected in the blood vessel. As shown, the image 200 is obtained prior to contrast being inject into the blood vessel and after catheter 202 and guide wire 204 have been inserted into the vessel. Image 200 may show one or more blood vessels, the catheter 202, and guide wire 204. While FIG. 200 is an angiography image, the external imaging device may be, for example, a CT or MRI machine such that the images are CT or MRI images.

FIG. 2B illustrates the identification of a junction point 206 on image 200. The junction point 206 is the proximal point of the catheter within the vessel. According to some examples, imaging processing techniques, machine learning "(ML")", and/or artificial intelligence ("AI") may identify the junction point 206. In some examples, the wire mask module 122 and/or junction point detection module 123 may identify junction point 206. The wire mask module and/or junction point detection module may use image processing techniques, ML, and/or AI to identify junction point 206. For example, a trained AI network may be used to predict and/or identify the location of junction point 206. Junction point 206 may be the proximal point of the guide catheter 202.

Figure 3B:
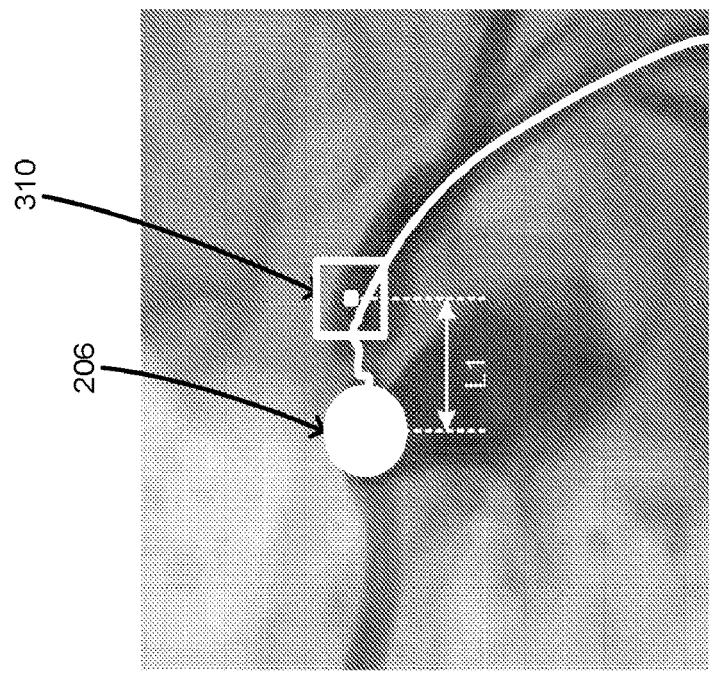
FIGS. 3A and 3B are example images annotated with intravascular data obtained during a first pullback according to aspects of the disclosure.
Figure 3A:
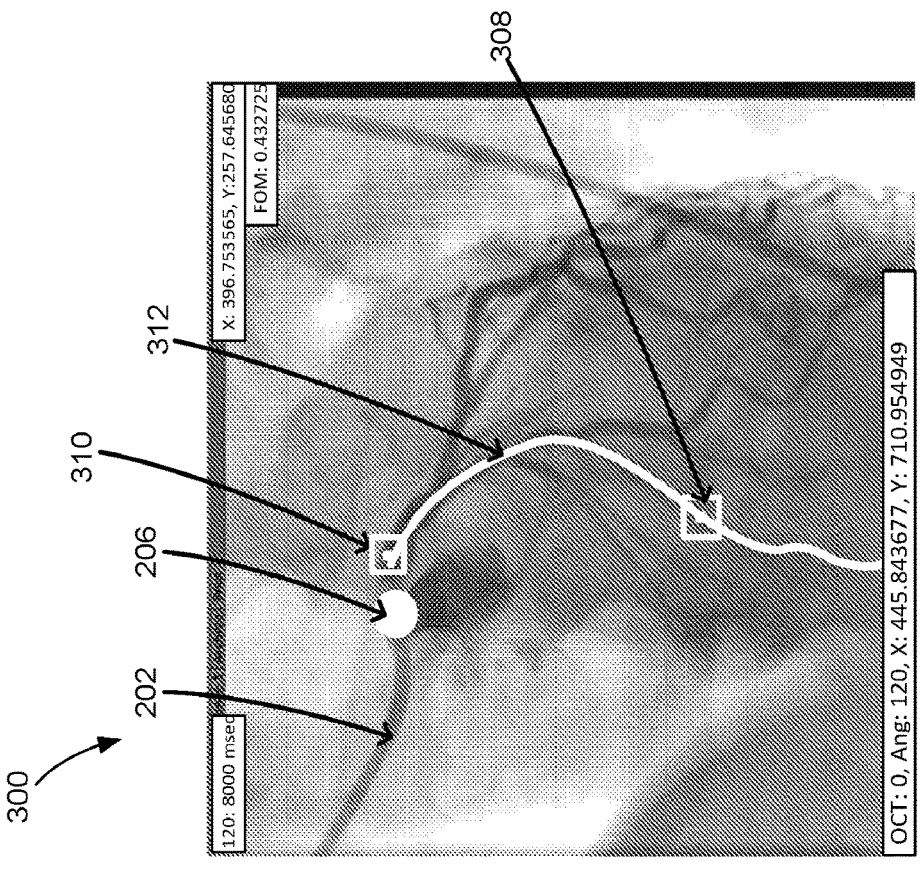

FIG. 3A illustrates an example of an image taken by an external imaging device in which the start and end points of a first pullback have been identified. Image 300 may be a composite image, such that one or more external images taken during the pullback have been combined and/or superimposed with each other to be able to identify the start and end point of the first pullback. According to some examples, contrast may be injected prior to and/or during the first pullback. The contrast may enhance, identify, and/or be used to detect the vascular structure in the region of interest.

As shown, image 300 shows the location of the catheter 202, the junction point 206, and details regarding the first pullback. The location of catheter 202 and junction point 206 in image 300, taken during the first pullback, may correspond or substantially correspond to the location of catheter 202 and junction point 206 in image 200, taken before the pullback. That is, the catheter 202 and, therefore, the junction point 206 does not change its position or location within the blood vessel once catheter 202 is inserted into the blood vessel. The details regarding the first pullback may include the start point, or distal point 308, of the first pullback, the end point, or proximal point 310, of the first pullback, and the trace 312, or path, of the pullback. The proximal point 310, distal point 308, and trace 312 may be identified, for example, by determining a wire mask image frame for each image frame. As described above, the wire mask module 122 may determine and/or create a wire mask image frame. The wire mask image frame may identify, highlight, or extract proximal point 310 of the pullback, distal point 308 of the pullback, trace 312, catheter 202, junction point 206, and/or radiopaque markers (not shown) on the probe or along trace 312 image 300.

According to some examples, image 300 may be a co-registered image. For example, image data recorded by the external imaging device 120 may be co-registered with intravascular data recorded by collection probe 104. The collection probe 104 may be, for example, an OCT probe, IVUS probe, pressure wire, micro-OCT probe, NIRS sensor, etc. In some examples the image data recorded by the external imaging device 120 may be angiographic images and the intravascular data recorded by the collection probe 104 may be OCT images, IVUS images, pressure readings from a pressure wire, etc. The intravascular data being recorded by collection probe 104 may be displayed as part of a graphic user interface. The intravascular data may be recorded at a certain location within the vessel. The extraluminal image recorded by the external imaging device 120 may include the location at which the intravascular data was recorded. The intravascular data may be related to the extraluminal image such the intravascular data and the extraluminal image display the same vessel segment with different views and/or data.

FIG. 3B illustrates the distance between the junction point 206 and the proximal point 310 of the first pullback. The distance "L1" may be automatically determined based on the identified junction point 206 and proximal point 310. For example, the location of junction point 206 in image 300 may be determined and/or identified by the trained AI network and the location of the proximal point 310 of the first pullback in image 300 may be identified by the wire mask module 122. Knowing the location of junction point 206 and proximal point 310 in image 300, a distance between the junction point 206 and proximal point 310 may be determined. The distance may be measured, for example, in pixels.

Figure 4B:
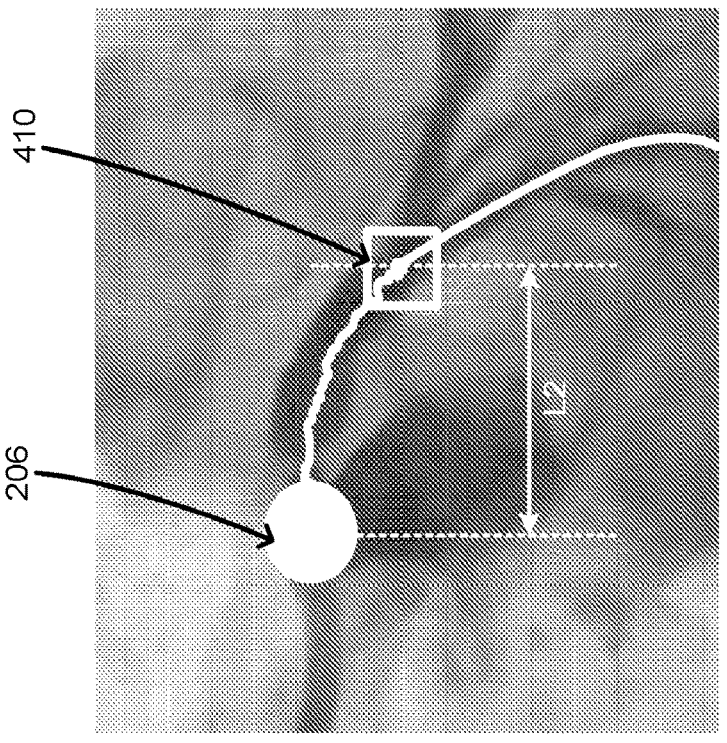
FIGS. 4A and 4B are example images annotated with intravascular data obtained during a second pullback according to aspects of the disclosure.
Figure 4A:
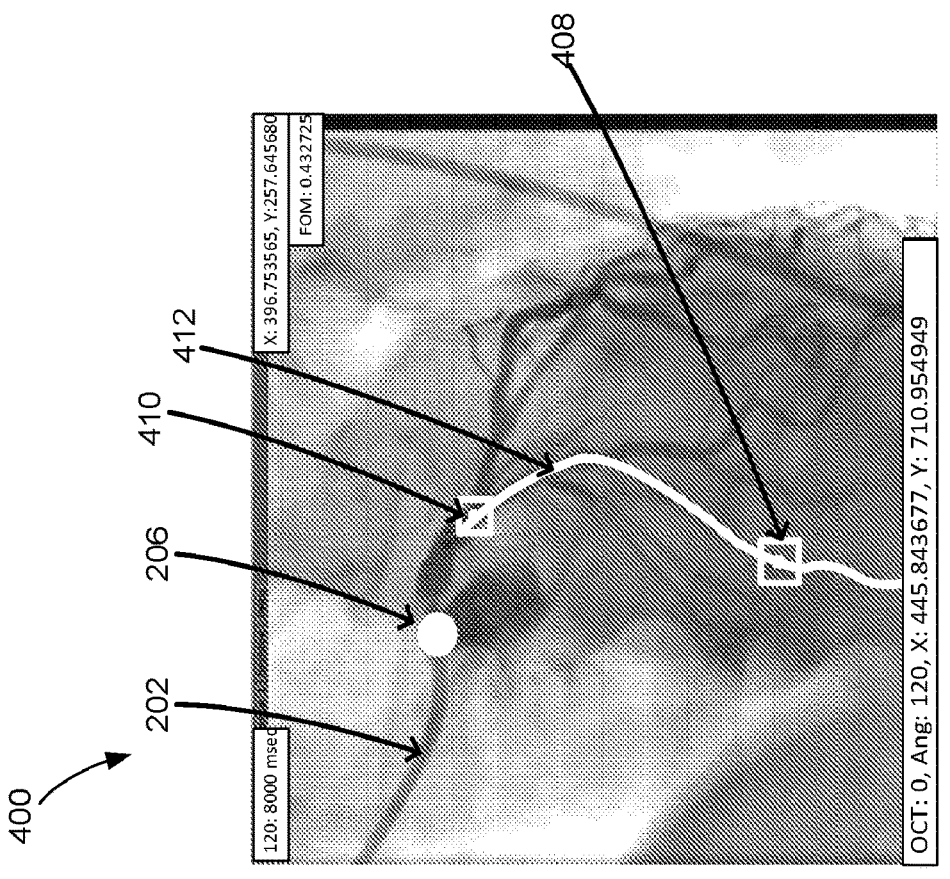

FIG. 4A illustrates an example of an image taken by the external imaging device in which the start and end points of a second pullback have been identified. Image 400 may be a composite image of a plurality of external images taken during the second pullback of an intravascular device. The second pullback may be completed using the same intravascular device or a different intravascular device than was used during the first pullback. For example, the first pullback may have used an OCT imaging probe while the second pullback may have used an IVUS imaging probe or a pressure wire.

According to some examples, the first pullback may be taken before any pre-coronary intervention ("PCI") is taken while the second pullback may be taken after PCI. In some examples, both the first and second pullbacks may occur before PCI or after PCI. For example, where the first pullback records OCT images and the second pullback records pressure measurements, both the first and second pullbacks may occur before and/or after PCI to be able to co-register pre- and/or post-PCI information.

Image 400 may identify catheter 202 and junction point 206. Catheter 202 and junction point 206 may be in the same position or location within blood vessel as in images 200, 300. That is, the location or position of catheter 202 may not change after being inserted into the blood vessel and/or after a first pullback. Image 400 may additionally or alternatively identify distal point 408, proximal point 410, and trace 412 of the second pullback. The distal point 408, proximal point 408, and trace 412 may be identified, for example, by determining a wire mask image frame.

FIG. 4B illustrates the distance between the junction point 206 and the proximal point 410 of second first pullback. The distance "L2" may be automatically determined based on the identified junction point 206 and proximal point 410. The distance "L2" may be more, less, or equal to the distance "L1."

Figure 5:
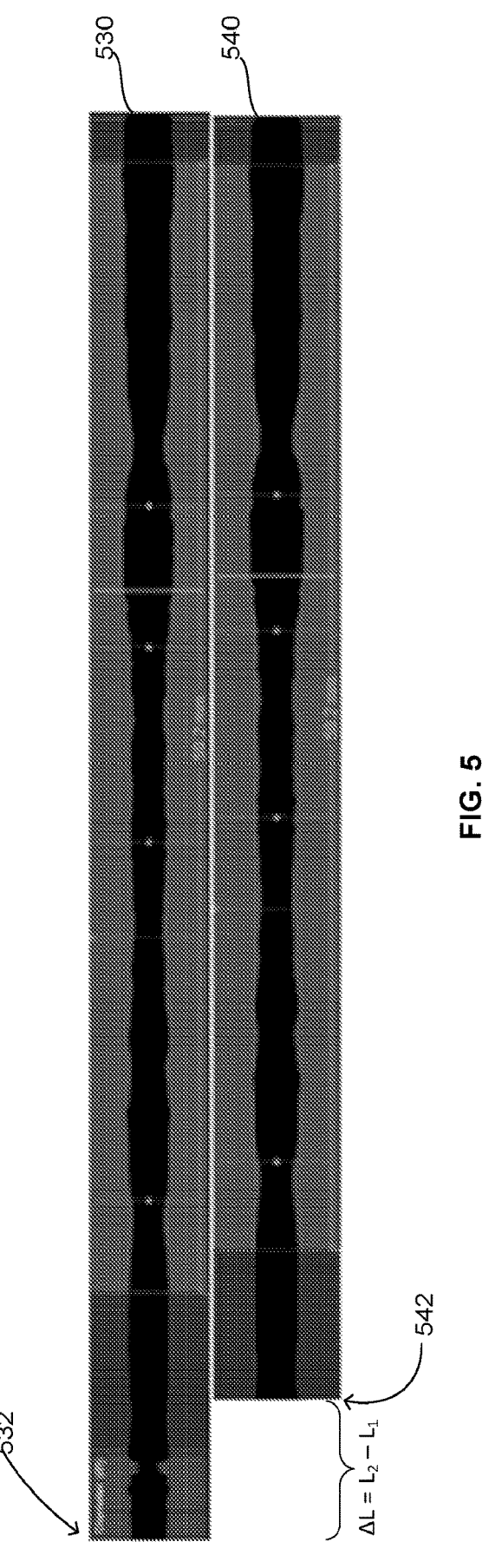
FIG. 5 is an example alignment of a representation of the intravascular data obtained during the first pullback and a representation of the intravascular data obtained during the second pullback according to aspects of the disclosure.

FIG. 5 illustrates an alignment of a first representation of the intravascular data received during the first pullback and a second representation of intravascular data received during the second pullback. As shown, the first and second representations are each longitudinal representations of the vessel. However, if the first and second pullbacks are different modalities, such as a first pullback of an OCT probe and a second pullback of a pressure wire, the first representation may be a longitudinal representation of the vessel and the second representation may be a graphical representation of the pressure within the vessel. According to some examples, the different modalities may be an OCT probe, IVUS probe, pressure wire, micro-OCT probe, NIRS sensor, etc. The first representation and the second representation may be vertically and/or horizontally aligned based a difference between the first distance "L1" and the second distance "L2."

As shown in FIG. 5, the first longitudinal representation 530 and the second longitudinal representation 540 may be vertically aligned such that a portion of the vessel in the first longitudinal representation 530 is vertically aligned with the same portion of the vessel in the second longitudinal representation 540. The second longitudinal representation 540 may be horizontally offset from the first longitudinal representation 530 by an offset distance. The offset difference may be the difference "ΔL" between the second distance "L2" and the first distance "L1." For example, the difference "ΔL" may be the difference between the distance from junction point 206 to proximal point 410 and the distance from junction point 206 to proximal point 310. Therefore, the proximal end 542 of the second longitudinal representation 540 may be horizontally offset from the proximal end 532 of the first longitudinal representation 530 by the difference "ΔL." The proximal end 542 of the second longitudinal representation 540 may correspond to proximal point 410 of the second pullback and proximal end 532 of the first longitudinal representation 530 may correspond to proximal point 310 of the first pullback.

According to some examples, the first pullback may occur before a user or physician performs any percutaneous coronary intervention ("PCI"). For example, the first pullback may be performed to receive intravascular data prior to any PCI in order for the physician to determine whether any additional testing and/or measurements are needed or to determine an appropriate intervention. The second pullback may be performed to obtain additional measurements. In some examples, the second pullback may be taken after PCI. By keeping the catheter in the same location within the vessel, the first and second pullbacks can be automatically aligned. The automatic alignment of the first and second pullbacks may allow the physician to easily see and/or compare the intravascular data from the first and second pullbacks without providing any user input.

FIG. 6 illustrates an example method of automatically aligning a first and second pullback. The following operations do not have to be performed in the precise order described below. Rather, various operations can be handled in a different order or simultaneously, and operations may be added or omitted.

For example, in block 610, the system may receive a plurality of extraluminal images of a target blood vessel. The extraluminal images may be, for example, angiographic images. According to some examples, the extraluminal images may be taken after a guide catheter is inserted into the target blood vessel.

In block 620, the system may detect a junction point in the plurality of extraluminal images. The junction point may be the proximal point of the guide catheter. In some examples, the junction point may be the location where the guide catheter meets the guide wire. The system may detect the junction point using a trained AI network. The trained AI network may output an AI mask for each of the extraluminal images. The AI mask may identify, highlight, or extract the guidewire, guide catheter, junction point, and/or radiopaque markers on the probe or guidewire.

In block 630, the system may receive a first set of intravascular data taken during a first pullback of a first intravascular device. The intravascular data may be recorded by an OCT probe, IVUS probe, pressure wire, micro-OCT probe, NIRS sensor, etc. The first pullback may have a start point and an end point. The start point may be the distal point of the pullback and the end point may be the proximal point of the pullback. According to some examples, the system may determine the proximal point and/or distal point of the pullback by determining and/or creating a wire mask image frame. The intravascular data may be, for example, intravascular images, pressure measurements, flow measurements, etc.

In block 640, the system may determine a first distance between the junction point and a first proximal end point of the first pullback. For example, the system may determine the distance between the end of the first pullback and the proximal end of the guide catheter.

In block 650, the system may receive a second set of intravascular data taken during a second pullback of a second intravascular device. According to some examples, the first and second intravascular devices may be the same intravascular device. In another example, the first and second intravascular devices may be different intravascular devices. In such an example, the first intravascular device may be an OCT probe and the second intravascular device may be a pressure wire.

According to some examples, the first pullback may occur before PCI and the second pullback may occur after PCI. In some examples, both the first and second pullbacks may occur before or after PCI.

In block 660, the system may determine a second distance between the junction point and a second distal end point of the second pullback. For example, the system may determine the distance between the end of the second pullback and the proximal end of the guide catheter.

In block 670, the system may align a first representation of the first pullback and a second representation of the second pullback. Aligning the first representation and the second representation may include determining a difference between the second distance and the first difference and offsetting, based on the determined different, the distal end of the second pullback from the distal end of the first pullback. For example, the first and second representations may each be output for display as a longitudinal representation. The first longitudinal representation of the first pullback may be vertically aligned with the second longitudinal representation of the second pullback. The distal end of the second representation may be offset, or horizontally shifted, with respect to the distal end of the first representation. According to other examples, the proximal end of the second representation may be offset from the proximal end of the first representation. The offset may be the difference between the second distance and the first distance.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value. All numerical values and ranges disclosed herein are deemed to include "about" before each value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The invention claimed is:

1. A method, comprising:
receiving, by one or more processors, a plurality of extraluminal images of a target blood vessel;
detecting, by the one or more processors, a junction point in the plurality of extraluminal images;
receiving, by the one or more processors, a first set of intravascular data taken during a first pullback of a first intravascular device;
determining, by the one or more processors, a first distance between the junction point and a first distal end point of the first pullback;
receiving, by the one or more processors, a second set of intravascular data taken during a second pullback of a second intravascular device;
determining, by the one or more processors, a second distance between the junction point and a second distal end point of the second pullback; and
aligning, by the one or more processors based on the first distance and the second distance, a first representation of the first set of intravascular data with a second representation of the second set of intravascular data.

2. The method of claim 1, further comprising outputting for display, by the one or more processors, the first representation and the second representation, wherein first representation is vertically aligned with the second representation.

3. The method of claim 1, wherein aligning the first representation and the second representation further includes:
determining, by the one or more processors, a difference between the second distance and the first distance; and
horizontally offsetting, by the one or more processors based on the determined difference, a distal end of the second representation from a distal end of the first representation.

4. The method of claim 1, wherein the junction point is a proximal point of a guide catheter.

5. The method of claim 1, wherein the first intravascular device is the same device as the second intravascular device.

6. The method of claim 1, wherein the first and second sets of intravascular data include intravascular images.

7. The method of claim 1, wherein the plurality of extraluminal images are taken during both the first pullback and the second pullback.

8. The method of claim 7, wherein detecting the junction point further includes determining, by the one or more processors based on the plurality of extraluminal images, the first set of intravascular data, or the second set of intravascular data, at least one artificial intelligence ("AI") mask.

9. The method of claim 1, wherein determining the first distal end point of the first pullback and the second distal end point of the second pullback further includes determining, based on the plurality of extraluminal images, the first set of intravascular data, or the second set of intravascular data, at least one wire mask image frame.

10. The method of claim 1, further comprising co-registering, by the one or more processors, the first set of intravascular data and the second set of intravascular data to the plurality of extraluminal images.

11. A device, comprising:
one or more processors, the one or more processors configured to:
receive a plurality of extraluminal images of a target blood vessel;

detect a junction point in the plurality of extraluminal images;

receive a first set of intravascular data taken during a first pullback of a first intravascular device;

determine a first distance between the junction point and a first distal end point of the first pullback;

receive a second set of intravascular data taken during a second pullback of a second intravascular device;

determine a second distance between the junction point and a second distal end point of the second pullback; and align, based on the first distance and the second distance, a first representation of the first set of intravascular data with a second representation of the second set of intravascular data.

12. The device of claim 11, wherein the one or more processors are further configured to output for display the first representation and the second representation, wherein first representation is vertically aligned with the second representation.

13. The device of claim 11, when wherein aligning the first representation and the second representation the one or more processors are further configured to:

determine a difference between the second distance and the first distance; and horizontally offset, based on the determined difference, a distal end of the second representation from a distal end of the first representation.

14. The device of claim 11, wherein the junction point is a proximal point of a guide catheter.

15. The device of claim 11, wherein the first intravascular device is the same device as the second intravascular device.

16. The device of claim 11, wherein the first and second sets of intravascular data include intravascular images.

17. The device of claim 11, wherein the plurality of extraluminal images are taken during both the first pullback and the second pullback.

18. The device of claim 17, wherein when detecting the junction point the one or more processors are further configured to determine, based on the plurality of extraluminal images, the first set of intravascular data, or the second set of intravascular data, at least one artificial intelligence ("AI") mask.

19. The device of claim 11, wherein when determining the first distal end point of the first pullback and the second distal end point of the second pullback the one or more processors are further configured determine, based on the plurality of extraluminal images, the first set of intravascular data, or the second set of intravascular data, at least one wire mask image frame.

20. The device of claim 11, wherein the one or more processors are further configured to co-register the first set of intravascular data and the second set of intravascular data to the plurality of extraluminal images.

* * * * *